(12) United States Patent
Yu et al.

(10) Patent No.: US 8,032,308 B2
(45) Date of Patent: Oct. 4, 2011

(54) MODELING LUNG CANCER SURVIVAL PROBABILITY AFTER OR SIDE-EFFECTS FROM THERAPY

(75) Inventors: Shipeng Yu, Exton, PA (US); Glenn Fung, Madison, WI (US); Cary Dehing-Oberije, Brunssum (NL); Dirk de Ruysscher, Tervuren (BE); Sriram Krishnan, Exton, PA (US); R. Bharat Rao, Berwyn, PA (US); Philippe Lambin, Genappe-Bousval (BE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/399,274

(22) Filed: Mar. 6, 2009

(65) Prior Publication Data
US 2009/0234627 A1 Sep. 17, 2009

Related U.S. Application Data

(60) Provisional application No. 61/038,202, filed on Mar. 20, 2008, provisional application No. 61/036,273, filed on Mar. 13, 2008.

(51) Int. Cl.
*G01N 33/48* (2006.01)
*G01N 33/50* (2006.01)
(52) U.S. Cl. ............................................. 702/19; 703/11
(58) Field of Classification Search .................... None
See application file for complete search history.

(56) References Cited

U.S. PATENT DOCUMENTS
7,844,560 B2 11/2010 Krishnan et al.
2003/0017481 A1* 1/2003 Golub et al. ................... 435/6
2003/0120458 A1 6/2003 Rao et al.

OTHER PUBLICATIONS

Mahler et al. Air-fluid levels within lung bullae associated with pneumonitis Lung, vol. 159, No. 1, 163-171, 1981.*
Aronberg et al. Lung carcinoma associated with bullous lung disease in young men. American Journal of Roentgenology, vol. 134, Issue 2, 249-252.*
Logan, M. AJR:171, 569-577,1998.*
Stanley et al. JNC3, vol. 63, No. 1, 25-32, 1980.*
Ball et al, "Failure of T stage to predict survival in patients with non-small-cell lung cancer treated by radiotherapy with or without concomitant chemotherapy", Int J Radiat Oncol Biol Phys 54:1007-13, 2002.
Bradley et al, "Gross tumor volume, critical prognostic factor in patients treated with three-dimensional conformal radiation therapy for non-small-cell lung carcinoma", Int J Radiat Oncol Biol Phys 52:49-57, 2002.
Dehing-Oberije et al, "Tumor volume combined with number of positive lymph node stations is a more important prognostic factor than TNM stage for survival of non-small-cell lung cancer patients treated with (chemo)radiotherapy", Int J Radiat Oncol Biol Phys 70:1039-44, 2008.
Brundage et al., "Prognostic factors in non-small cell lung cancer: a decade of progress", Chest 122:1037-57, 2002.
Pfister et al., "American Society of Clinical Oncology treatment of unresectable non-small-cell lung cancer guideline: update 2003", J Clin Oncol 22:330-53, 2004.
Firat et al., "Performance score are independent prognostic factors in stage III non-small-cell lung cancer: an institutional analysis of patients treated on four RTOG studies", Radiation Therapy Oncology Group. Int J Radiat Oncol Biol Phys 54:357-64, 2002.
"Chemotherapy for non-small cell lung cancer", Non-small Cell Lung Cancer Collaborative Group. Cochrane Database Syst Rev:CD002139, 2000.
Basaki et al, "Prognostic factors for survival in stage III non-small-cell lung cancer treated with definitive radiation therapy: impact of tumor volume", Int J Radiat Oncol Biol Phys 64:449-54, 2006.
Werner-Wasik et al., "Increasing Tumor Volume is Predictive of Poor Overall and Progression-Free Survival: Secondary Analysis of the Radiation Therapy Oncology Group 93-11 Phase I-II Radiation Dose-Escalation Study in Patients with Inoperable Non-Small-Cell Lung Cancer", Int J Radiat Oncol Biol Phys 70:385-90, 2008.
Zhao et al, "High radiation dose may reduce the negative effect of large gross tumor volume in patients with medically inoperable early-stage non-small cell lung cancer", Int J Radiat Oncol Biol Phys 68:103-10, 2007.
Solan et al., "Prognostic factors in non-small cell lung cancer". Semin Surg Oncol 21:64-73, 2003.
Wulfkuhle et al., "Genomic and proteomic technologies for individualisation and improvement of cancer treatment", Eur J Cancer 40:2623-32, 2004.
Boldrini et al., "Pognostic significance of osteopontin expession in early-stage non-small-cell lung cancer",Br J Cancer 93:453-7, 2005.
Donati et al, "Osteopontin expression and prognostic significance in non-small cell lung cancer", Clin Cancer Res 11:6459-65, 2005
Kaminska et al., "Pretreatment serum levels of cytokines and cytokine receptors in patients with non-small cell lung cancer, and correlations with clinicopathological features and prognosis. M-CSF—an independent prognostic factor", Oncology 70:115-25, 2006. .

(Continued)

Primary Examiner — Michael Borin
(74) Attorney, Agent, or Firm — Joshua B. Ryan (57) ABSTRACT

Modeling of prognosis of survivability, side-effect, or both is provided. For example, RILI is predicted using bullae information. The amount, volume or ratio of Bullae, even alone, may indicate the likelihood of complication, such as the likelihood of significant (e.g., stage 3) pneumonitis. As another example, RILI is predicted using uptake values of an imaging agent. Standardized uptake from a functional image (e.g., FDG uptake from a positron emission image), alone or in combination with other features, may indicate the likelihood of side-effect. In another example, survivability, such as two-year survivability, is predicted using blood biomarkers. The characteristics of a patient's blood may be measured and, alone or in combination with other features, may indicate the likelihood of survival. The modeling may be for survivability, side-effect, or both and may use one or more of the blood biomarker, uptake value, and bullae features.

11 Claims, 6 Drawing Sheets

OTHER PUBLICATIONS

Koukouraksi et al., "Lactate dehydrogenase-5 (LDH-5) overexpression in non-small-cell lung cancer tissues is linked to tumour hypoxia, angiogenic factor production and poor prognosis", Br J Cancer 89:877-85, 2003.

Le et al, "An evaluation of tumor oxygenation and gene expression in patients with early stage non-small cell lung cancers",Clin Cancer Res 12:1507-14, 2006.

Orditura et al., "Elevated serum levels of interleukin-8 in advanced non-small cell lung cancer patients: relationship with prognosis", J Interferon Cytokine Res 22:1129-35, 2002.

Songur et al., "Serum interleukin-6 levels correlate with malnutrition and survival in patients with advanced non-small cell lung cancer", Tumori 90:196-200, 2004.

Muley et al., "CYFRA 21-1 and CEA are independent prognostic factors in 153 operated stage I NSCLC patients", Anticancer Res 24:1953-6, 2004MU.

Pujol et al, "CYFRA 21-1 is a prognostic determinant in non-small-cell lung cancer: results of a meta-analysis in 2063 patients", Br J Cancer 90:2097-105, 2004.

Swinson et al, "Cabon anhydrase IX expression, a novel surrogate marker of tumor hypoxia, is assoicated with a poor prognosis in non-small-cell lung cancer", J Clin Oncol 21:473-82, 2003.

Sin et al.,"Systemic inflammation and mortality in chronic obstructive pulmonary disease", Can J Physicol , Pharmacol 85:141-7, 2007.

Cox et al, "Interruptions of high-dose radiation therapy decrease long-term survival of favorable patients with unresectable non-small cell carcinoma of the lung: analysis of 1244 cases" from 3 Radiation Therapy Oncology Group (RTOG) trials. Int J Radiat Oncol Biol Phys 27:493-8, 1993.

Burges, "A Tutorial on Support Vector Machines for Pattern Recognition", Kluwer Academic Publishers, Boston, MA pp. 1-43; Appeared in: Data Mining and Knowledge Discovery 2, 121-167, 1998.

Verduijn, et al., "Prognostic Bayesian Networks I: Rationale, Learning Procedure, and Clinical Use", Journal of Biomedical Informatics, 40(2007), pp. 607-618.

Peek, et al., "ProCarSur: A System for Dynamic Prognostic Reasoning in Cardiac Surge", AIME 2007, LNAI 4594, pp. 336-340, 2007.

Farhangfar, et al, "Impact of Imputation of Missing Values on Classification Error for Discrete Data", Pattern Recognition 41(2008) pp. 3692-3705.

Murphy, K., "Bayes Net Toolbox for Matlab", Oct 19, 2007, URL: http://www.cs.ubc.ca/murphyk/Software/BNT/bnt.

Murphy, K., "The Bayes Net Toolbox for Matlab", Computing Science and Statistics, vol. 33, No. 2 (Oct. 9, 2001), pp. 1024-1034.

Chickering, et al, "Large-Sample Learning of Bayesian Networks is NP-Hard", Journal of Machine Learning Research 5 (2004) pp. 1287-1330.

Dehing-Oberue, et al, "Development and External Validation of Prognostic Model for 2-Year Survival of Non-Small-Cell Lung Cancer Patients Treated with Chemoradiotherapy", Int. J. Radiation Oncology Biol. Phys., vol. 74, No. 2, pp. 355-362, 2009.

Eaton, et al, "Bayesian Structure Learning Using Dynamic Programming and MCMC", 2007 Proceedings of the 23rd Annual Conference on Uncertainty in Artificial Intelligence (UAI-07).

Lam, et al, "Learning Bayesian Belief Networks An Approach Based on the MDL Principle", 2nd Pacific Rim International Conference on Artificial Intelligence, 1992, pp. 1237-1243.

Fung, et al, "Finite Newton Method for Lagrangian Support Vector Machine Classification", Neurocomputing, vol. 55, Issues 1-2, Support Vector Machines, Sep. 2003, pp. 39-55.

Pelckmans, et al, "Handling Missing Values in Support Vector Machine Classifiers", Neural Networks, vol. 18, Issues 5-6, IJCNN 2005, Jul.-Aug. 2005, pp. 684-692.

Pillot, et al, "Prognostic Value of Fluorodeoxyglucose Positron Emission Tomography in Non-small Cell Lung Cancer: A Review", Journal of Thoracic Oncology, Feb. 2006, vol. 1, Issue 2, pp. 152-159.

Heckerman, et al, "Learning Bayesian networks: The combination of knowledge and statistical data", Machine Learning, vol. 20, No. 3, 197-243, 1995.

Burnside, ES, "Bayesian Networks: Computer-assisted Diagnosis Support in Radiology", Acad. Radiol. vol. 12, No. 4, pp. 422-430, Apr. 2005.

"Commonly Diagnosed Cancers Worldwide", Cancer Research UK (Apr. 2005).

Hoot, et al, "Bayesian Networks to Predict Survival of Liver Transplant Patients", AMIA Annu Symp Proc. 2005:345-349.

Needam, et al, "A Primer on Learning in Bayesian Networks for Computational Biology", PLoS Computational Biology, vol. 3, Issue 8, Aug. 2007, pp. 1409-1416.

Hartemink, et al, "Bayesian Methods for Elucidating Genetic Regulatory Networks", IEEE Intelligent Systems, 2002, pp. 37-43.

Lauritzen, S., "The EM Algorithm for Graphical Association Models with Missing Data", Computational Statistics & Data Analysis 19(1995) pp. 191-201.

* cited by examiner

MODELING LUNG CANCER SURVIVAL PROBABILITY AFTER OR SIDE-EFFECTS FROM THERAPY

RELATED APPLICATIONS

The present patent document claims the benefit of the filing dates under 35 U.S.C. §119(e) of Provisional U.S. Patent Application Ser. Nos. 61/038,202 and 61/036,273, filed Mar. 20, 2008 and Mar. 13, 2008, respectively, which are hereby incorporated by reference.

BACKGROUND

The present embodiments relate to modeling lung cancer survival after or side-effects from therapy.

Survival or survivability from lung cancer, such as non-small cell lung cancer (NSCLC), is relatively low as compared to some other cancers. One common treatment is surgery to resect tumors. Accordingly, various prognosis techniques are directed to patients to be treated with surgery. However, these techniques may not apply to lung cancer patients treated with radiation and/or chemotherapy.

Patients with stage I-IIIB lung cancer may be treated with curative intent without surgery. Currently, prediction of survival outcome for NSCLC patients treated with (chemo) radiotherapy is mainly based on clinical factors using TNM staging. However, clinical TNM staging may be inaccurate for survival prediction of non-surgical patients, and alternatives are currently lacking.

To improve risk stratification for non-surgical patients, a number of variables associated with survival have been identified. At present, the generally accepted prognostic factors for survival of inoperable patients are performance status, weight loss, presence of comorbidity, use of chemotherapy in addition to radiotherapy, and tumor size. Retrospective studies suggest that a higher radiation dose leads to improved local control and better survival rates. For other factors, such as sex and age, the literature shows inconsistent results, making it impossible to draw definitive conclusions.

In addition to difficulties predicting survivability, there are difficulties predicting side-effects from radiation. If radiation therapy is used to treat tumors in and around the thoracic region, such as lung and breast cancer, a commonly found side-effect is radiation-induced lung injury (RILI). Toxicity (i.e., RILI) of the respiratory system may result in significant morbidity, occurring in around 13% to 37% of patients with lung cancer. To predict of the risk of RILI in non-small cell lung cancer patients, dosimetric parameters, such as the mean lung dose (MLD) or volume of the lung receiving more than 20 Gy (V20), are used. However, the accuracy of dosimetric parameters is ususally low, resulting in AUC's of about 0.60.

Imaging may be used to assist in diagnosis or prognosis. For example, the volume of a tumor is used to predict survivability. Imaging may provide other general information used by medical professionals. For example, standardized uptake values (SUV) of an imaging agent may be used to measure inflammation of lung tissue.

SUMMARY

In various embodiments, systems, methods, instructions, and computer readable media are provided for modeling the treatment outcome of lung cancer patients. Prognosis of survivability, side-effects, or both is provided. For example, RILI is predicted using bullae information. The amount, volume or ratio of bullae, even alone, may indicate the likelihood of RILI, such as the likelihood of significant (e.g., grade 3) pneumonitis. As another example, RILI is predicted using standardized uptake values of an imaging agent. Standardized uptake from a functional image (e.g., FDG uptake from a positron emission image), alone or in combination with other features, may indicate the likelihood of side-effects. In another example, survivability, such as two-year survivability, is predicted using blood biomarkers. The characteristics of a patient's blood may be measured and, alone or in combination with other features, may indicate the likelihood of survival. The modeling may be for survivability, side-effects, or both and may use one or more of the blood biomarker, uptake value, and bullae features.

In a first aspect, a system is provided for modeling of lung cancer patients. An input is operable to receive lung cancer patient information representing blood biomarkers of a lung cancer patient, lung bullae of the lung cancer patient, uptake of an imaging agent of a lung of the cancer patient, or any combination thereof. A processor is operable to apply a model as a function of the lung cancer patient information. The model is operable to output side-effects prediction, survivability prediction, or both side-effects and survivability prediction for the lung cancer patient as a response to radiation therapy. A display is operable to output an image. This image indicates the side-effects prediction, survivability prediction, or both side-effects and survivability prediction output from the model for the lung cancer patient.

In a second aspect, a computer readable storage medium has stored therein data representing instructions executable by a programmed processor for modeling of lung cancer patients. The instructions include receiving bullae information for a patient with a lung tumor, predicting radiation-induced lung injury as a function of the bullae information for the patient, and outputting a likelihood of the radiation-induced lung injury as a function of the prediction.

In a third aspect, a computer readable storage medium has stored therein data representing instructions executable by a programmed processor for modeling of lung cancer patients. The instructions include receiving blood biomarker information for a patient with a lung tumor, predicting survivability of the patient after radiotherapy, the predicting being a function of the blood biomarker information for the patient, and outputting the survivability.

In a fourth aspect, a computer readable storage medium has stored therein data representing instructions executable by a programmed processor for modeling of lung cancer patients. The instructions include receiving information represent uptake of an imaging agent for a patient with a lung tumor, predicting radiation-induced lung injury as a function of the information representing the uptake for the patient, and outputting a likelihood of the radiation-induced lung injury as a function of the predicting.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

DESCRIPTION OF PREFERRED EMBODIMENTS

Different features may be identified and used for predicting side-effects or survivability. The features provide prediction models for survival or side-effects of non-small cell lung cancer (NSCLC) patients treated with radiotherapy with or without chemotherapy. Prognostic models are developed and validated for survival and side-effects of NSCLC patients treated with radiotherapy. These different features are addressed below separately, but may be used together.

Early prediction of radiation-induced lung injury (RILI) may use uptake patterns in the lung, such as FDG uptake. The FDG uptake in the lung, with or without other features, may reflect subclinical RILI and hence be predictive for later development of RILI. Uptake is acquired before therapy or early during radiotherapy to allow for alteration of the therapy based on the prediction.

Bullae-related information may be used for predicting radiation-induced lung injury (RILI). For example, the percentage of bullae predicts radiation-induced pneumonitis. The percentage of this non-functional tissue (i.e., air-filled cavities (bullae)) in the lung may improve significantly the prediction of acute RILI in particular.

Blood biomarkers, such as biomarkers related to hypoxia, acidosis, tumor load, and inflammation, may be used for predicting survivability. Blood biomarkers may have an added prognostic value for predicting survival. Other features may be used, such as sex, performance status, forced expiratory volume ($FEV_1$), number of positive lymph node stations (PLNS), and gross tumor volume (GTV), with the blood biomarkers for the prediction.

Figure 1:
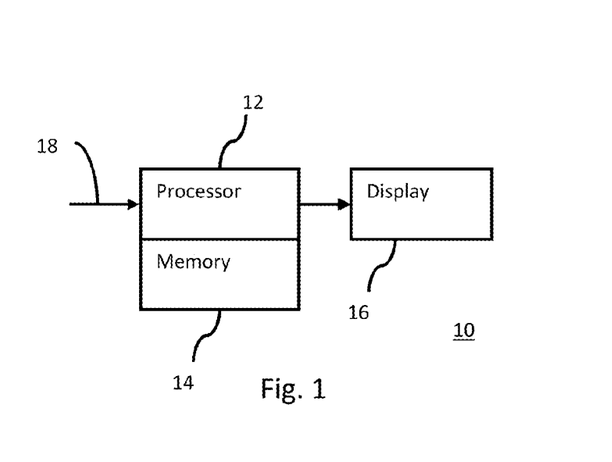
FIG. 1 is a block diagram of one embodiment of a system for modeling of lung cancer patients.

FIG. 1 shows a block diagram of an example system 10 for modeling of lung cancer patients. The system 10 is shown as a hardware device, but may be implemented in various forms of hardware, software, firmware, special purpose processors, or a combination thereof. Some embodiments are implemented in software as a program tangibly embodied on a program storage device. By implementing with a system or program, semi-automated workflows are provided to assist a user in generating a prediction of treatment outcome and/or recommending radiation dose. Data representing a patient is transformed into an image of data indicating side-effects or survivability of treatment. The system 10, using a machine, allows prediction for many patients and training of a model based on large data sets as compared to manual determination. For application, the system 10 transforms data representing characteristics of the patient into an output useable by doctors in treatment or therapy planning.

The system 10 is a computer, personal computer, server, PACs workstation, imaging system, medical system, network processor, network, or other now known or later developed processing system. The system 10 includes at least one processor (hereinafter processor) 12, at least one memory (hereinafter memory) 14, a display 16, and at least one input (hereinafter input) 18. Additional, different, or fewer components may be provided.

The processor 12 is implemented on a computer platform having hardware components. The computer platform also includes an operating system and microinstruction code. The various processes, methods, acts, and functions described herein may be either part of the microinstruction code or part of a program (or combination thereof) executed via the operating system.

The input 18 is a user input, network interface, external storage, or other input device for providing data to the system 10. For example, the input 18 is a mouse, keyboard, track ball, touch screen, joystick, touch pad, buttons, knobs, sliders, combinations thereof, or other now known or later developed user input device. The user input may operate as part of a user interface. For example, one or more buttons are displayed on the display 16. The user input is used to control a pointer for selection and activation of the functions associated with the buttons. Alternatively, hard coded or fixed buttons may be used. As another example, the input 18 is a hard-wired or wireless network interface. A universal asynchronous receiver/transmitter (UART), a parallel digital interface, a software interface, Ethernet, or any combination of known or later developed software and hardware interfaces may be used. The network interface may be linked to various types of networks, including a local area network (LAN), a wide area network (WAN), an intranet, a virtual private network (VPN), and the Internet.

The input 18 is an interface to receive data. The data may include clinical information, such as the age, gender, family history, test results, tumor volume, or other information determined to be relevant to the treatment of a tumor and/or prediction. The data may include blood biomarkers, lung bullae, uptake, or other imaging or test information. Combinations of information may be received, such as both blood biomarkers and uptake information. Any combination of information may be used. Any derived quantities or raw data may be used, such as a lung volume being provided on the input 18 or an image for deriving lung volume being provided on the input 18.

In one embodiment, the input 18 receives lung cancer patient information representing blood biomarkers. Using now known or later developed blood tests, biomarkers of a lung cancer patient are obtained. The biomarkers are represented by data.

In another embodiment, the input 18 receives lung cancer patient information representing lung bullae. The lung cancer patient has a volume, number, average size, median size, area, locations, or other characteristics of bullae. One or more of these characteristics or a quantity derived from one or more of these characteristics are received on the input 18. For example, a percentage of the lungs occupied by bullae for a patient is received. As another example, the volume of the bullae and the lung volume are received. In another example, an image, which includes bullae information, is received.

Figure 2:
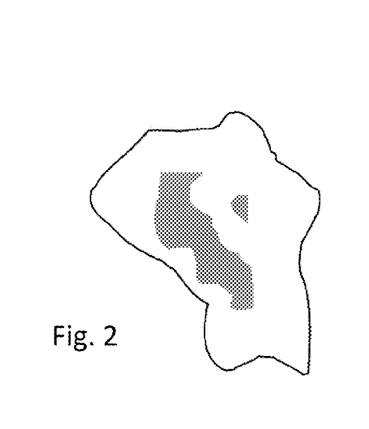
FIG. 2 illustrates an example tumor with distribution of uptake values.

In yet another embodiment, the input 18 receives lung cancer patient information representing uptake of an imaging agent. For example, the uptake of the imaging agent is reflected in functional imaging data. Uptake for functional imaging information includes an image, data to generate an image, quantities derived from a functional scan, or other data that is a function of functional imaging data. Functional imaging data represents metabolic or biochemical activity of a tumor. For example, positron emission tomography is used with fluorodeoxyglucose (FDG) for scanning a non-small cell lung cancer tumor. The FDG is taken up by the tissue, showing glucose metabolism in the PET data. FIG. 2 shows an example tumor with darker areas highlighted as having high uptake values. "Uptake" is used to reflect binding, absorption, tagging, labeling, connecting, or other reaction of an agent to the tissue. Other now known or later developed functional imaging modes may be used. Other now known or later developed imaging agents to identify function in the scan region may be used. In alternative embodiments, the imaging modality identifies tissue function based on data processing without introduction of a contrast or binding agent.

In one embodiment, PET-FDG data is acquired with a CT-PET imaging system. The imaging system generates both CT and PET information for at least an overlapping region. The CT scan provides structural information, such as the location of ribs or bones. Since the scans are performed with the same system and close in time, the relative position of the PET scan to the CT scan is known. Correlation processing may alternatively be used to spatially align functional data with structural data. In other embodiments, manual alignment is provided, or the functional data is used without alignment with structural data. Other combinations of imaging modes may be used, such as MRI-PET.

The CT data may be used to spatially align PET-CT scans from different times. The data from different times may show a change in uptake. For example, uptake is measured before treatment and again during treatment, such as 7-14 days after starting the treatment. Other periods may be used. For predicting injury or survivability, shorter periods may provide for more opportunity to modify therapy according to the corresponding predictions. The change in uptake or images to derive the change in uptake may be received on the input 18. Change may be reflected by change in volume of uptake, change in area, change in average, change in number of regions, or other parameter.

The processor 12 has any suitable architecture, such as a general processor, central processing unit, digital signal processor, application specific integrated circuit, field programmable gate array, digital circuit, analog circuit, combinations thereof, or any other now known or later developed device for processing data. Likewise, processing strategies may include multiprocessing, multitasking, parallel processing, and the like. A program may be uploaded to, and executed by, the processor 12. The processor 12 implements the program alone or includes multiple processors in a network or system for parallel or sequential processing.

The processor 12 creates a model, applies the model, or both creates and applies the model. The model is of survivability and/or side-effects in response to radiation therapy. The model may or may not account for the radiation plan, such as the MLD or other dose parameter.

In one embodiment, the model is a machine-learned model. For example, a model predicting survivability from blood biomarkers is machine trained. As another example, a model predicting injury from uptake information is machine trained. Any machine-learning algorithm or approach to classification may be used. For example, a support vector machine (e.g., 2-norm SVM), linear regression, boosting network, linear discriminant analysis, relevance vector machine, combinations thereof, or other now known or later developed machine learning is provided. The machine learning provides a matrix or other output. The matrix is derived from analysis of a database of training data with known results, such as a database of data with binary or a larger range of possible labeled outcomes. The machine-learning algorithm determines the relationship of different inputs to the result. The learning may select only a sub-set of input features or may use all available input features. A programmer may influence or control which input features to use or other performance of the training. For example, the programmer may control the amount of variance or smoothness of a hyperplane or line in SVM training. The matrix associates input features with outcomes, providing a model for classifying. Machine training provides relationships using one or more input variables with outcome, allowing for verification or creation of interrelationships not easily performed manually.

Alternatively, manually programmed models may be used. For example, a model predicting injury from only bullae information is programmed. The model may be validated using machine training.

The model represents a probability of survivability, side-effects, or both. This probability is a likelihood for the disease of interest, such as non-small cell lung cancer. The likelihood is modeled from any lung cancer patient information. Any limitation may be used, such as a one-year, two year, three year or other term of survival. For example, the model predicts the likelihood of grade three as opposed to all other (no, grade one and grade two) grades of pneumonitis. Other probabilities may be used. Any period may be used for measuring whether injury has occurred, such as 90 days after completion of treatment. Alternatively, the probability is based on measurements during treatment, such as for reoccurrence or after exposure to a partial dose.

Different probabilities may be learned based on the input or output levels. The possible values may be grouped, such that a different model is provided for different input ranges and/or output possibilities. For example, probability of injury is determined for each of four possible grades. More or fewer levels of increment may be provided. Each probability indicates the likelihood of injury at a certain level (e.g., probability x for grade 3, y for grade 2, w for grade 1, and u for no injury where each probability is based on a different model).

The probability is learned or derived from data of other patients, training data. The database of other patients includes clinical, imaging, and/or other data from before therapy and at the desired time after or during therapy. The dose applied to the tumor and/or regions of the tumor for treatment may be included. Other features may be provided, such as age, gender, WHO performance, lung function (e.g., expiration volume), tumor type, and tumor size. Different feature vectors may be provided for different types of tumors, different models, and/or different probabilities (e.g., side-effects versus survival).

For the training data, injury is measured subjectively, such as by a medical practitioner, or objectively, such as by the results of a test. Tissue or an image may be examined for pneumonitis or other injury. Alternatively, the processor 12 determines injury. For example, CT image information is analyzed to identify injured segments or regions. For survival training data, user entry of the binary indication of survival is used. Alternatively, the survival information is mined from other sources by the processor 12.

The functional imaging (e.g., uptake values) or other input feature information may be normalized. For example, uptake values are normalized based on uptake for healthy tissue. The normalized uptake values provide standardized uptake values (SUV). The SUV at a given time may be an integral of the SUV over all the voxels of a tumor. A change in SUV is determined by a difference between the integrals of SUV. The model is trained based on the difference in SUV, but may use other SUV parameters.

The processor 12 applies the model or models. The uptake values, blood biomarkers, bullae information, clinical information, dose, and/or other data of relevant feature vectors is input into the model or models. The information may be input according to requirements, such as inputting values in specific units. Alternatively, raw data is input and the model includes preprocessing to derive the values used to train the model. For example, a ratio of lung bullae to a lung volume is determined from input CT image data.

Different inputs may be used for different models. For example, survivability is predicted using a feature vector including multiple blood biomarkers, clinical data, and dose. As another example, RILI is predicted from only bullae information, such as only a percentage of the lung occupied by bullae. Missing data may be substituted with an average, median, default value, or an expectation based on other inputs, or more sophisticated models may be used to impute missing data. Alternatively, missing data may be left blank where the model may still provide sufficient accuracy.

In response to the input, the model outputs a probability. The output is a side-effect prediction. For example, the likelihood of a patient suffering from pneumonitis is output. Alternatively or additionally, the output is a survivability prediction. For example, the likelihood of a patient surviving for two years after treatment is output. The processor 12 outputs the probability or probabilities for creating or using the models. The processor 12 outputs the data to the memory 14, over or to a network, to a printer, or in other media.

The output and/or inputs may be displayed to a user on the display 16. The display 16 is a CRT, LCD, plasma, projector, monitor, printer, or other output device for showing data. The display 16 is operable to display an image. The image may be of a medical image, a user interface, charts, graphs, values, or other information, such as the side-effects prediction, survivability prediction, or both. For example, the display 16 outputs an image generated with information output from the model for the lung cancer patient. The image shows the predicted likelihood with or without other information. The likelihood is based on data specific to or representing a given patient. More than one likelihood may be output, such as a graph representing the probability of survival as a function of time or the probability of side-effect as a function of dose. The display is text, graphical, or other display. Supporting information, such as values, different model outputs, options, or other supporting information, may be displayed.

The processor 12 operates pursuant to instructions. The instructions, model, matrix, image data, clinical data, blood biomarkers, bullae data, uptake data, and/or patient record for modeling of lung cancer patients are stored in a computer readable memory, such as external storage, memory 14 (e.g., cache, system memory, ROM and/or RAM). The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Because some of the constituent system components and method acts depicted in the accompanying figures may be implemented in software, the actual connections between the system components (or the process steps) may differ depending upon the manner of programming.

The same or different computer readable media may be used for the instructions, the individual patient data, the model, and the database of previously treated patients (e.g., training data). The patient records are stored in the external storage, but may be in other memories. The external storage or the memory 14 may be implemented using a database management system (DBMS) managed by the processor 12 and residing on a memory, such as a hard disk, RAM, or removable media. The external storage may be implemented on one or more additional computer systems. For example, the external storage may include a data warehouse system residing on a separate computer system, a PACS system, or any other now known or later developed hospital, medical institution, medical office, testing facility, pharmacy or other medical patient record storage system. The external storage, an internal storage (memory 14), other computer readable media, or combinations thereof store data for at least one patient record for a patient. The patient record data may be distributed among multiple storage devices.

In other embodiments, the system 10 connects with a structural imaging system, a functional imaging system, a blood testing system, and/or a therapy applicator (e.g., linear accelerator). For example, the system 10 connects with a CT-PET system and a linear accelerator for radiation therapy. The imaging system scans the patient and provides data representing the scanned region of the patient for transformation by analysis. As another example, the system 10 connects with a blood testing system or database from a blood testing facility. The data is provided for transformation by modeling. The system 10 assists the user in planning therapy. The output information may be used to select between receiving radiation therapy or not and/or to select appropriate dose. The system 10 is part of one of these components and/or communicates with the components to acquire image data and control treatment. For example, the processor 12 communicates a fraction of a treatment plan to the linear accelerator, controlling application of radiation to the patient.

Figure 3:
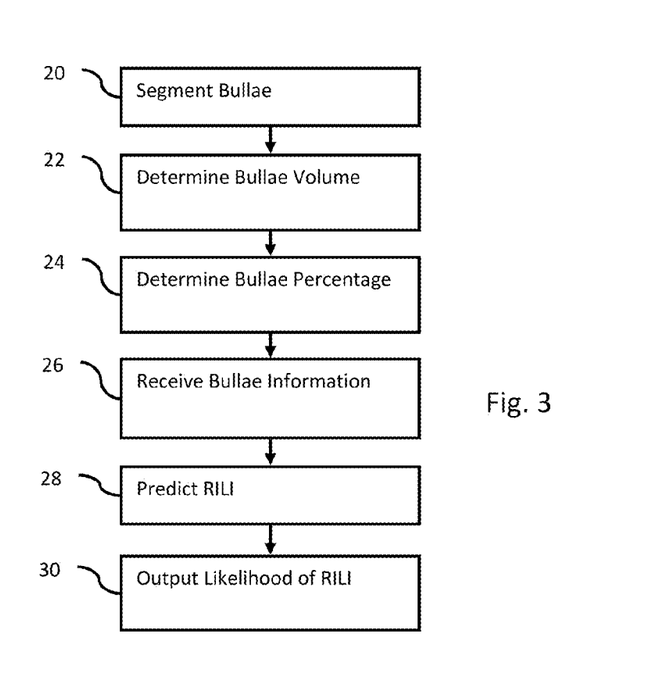
FIG. 3 is a flow chart diagram of one embodiment of a method for modeling of lung cancer patients using Bullae information.
Figure 4:
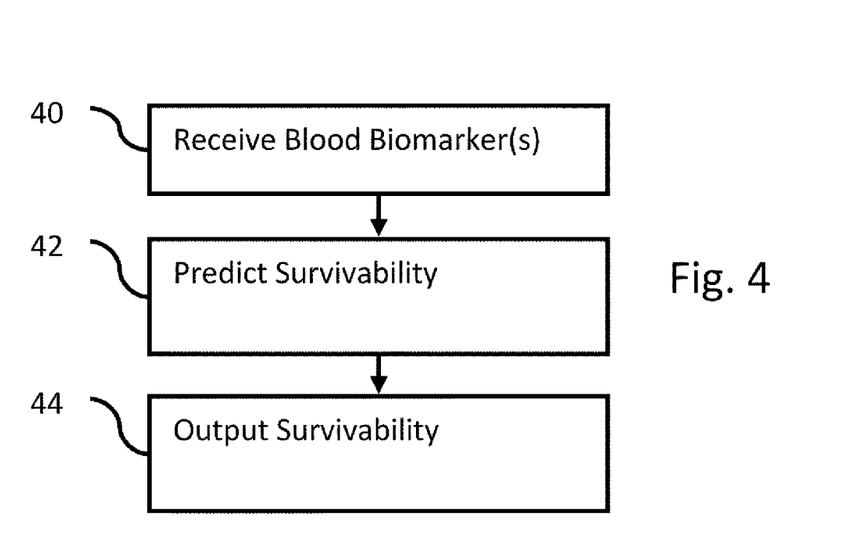
FIG. 4 is a flow chart diagram of one embodiment of a method for modeling of lung cancer patients using a blood biomarker.
Figure 5:
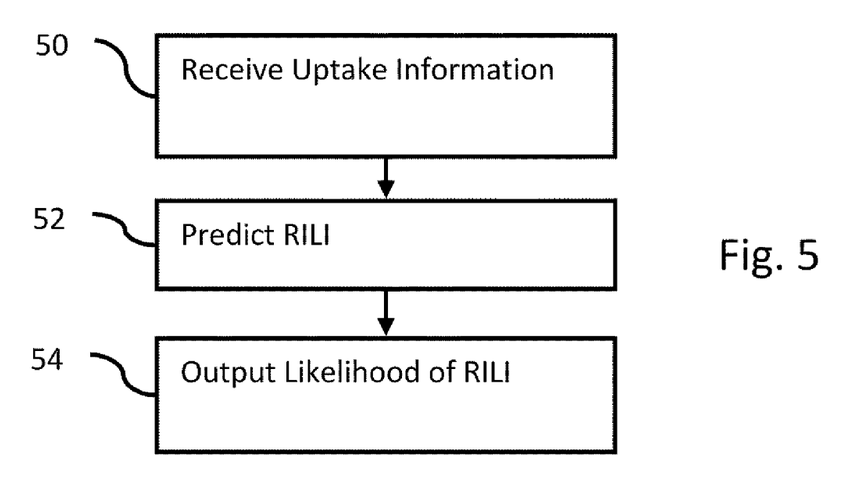
FIG. 5 is a flow chart diagram of one embodiment of a method for modeling of lung cancer patients using uptake values.

FIGS. 3-5 show methods for modeling of a lung cancer patient. FIGS. 3-5 are first described in common. Specific models for each of FIGS. 3-5 are then described.

The models are created and/or applied using patient information, including bullae information (FIG. 3), blood biomarker information (FIG. 4), and uptake information (FIG. 5). Any other patient information may be used, such as clinical characteristics, treatment, imaging, tumor and/or other information. Patient clinical characteristics may include age, gender, co-morbidities, performance score (WHO, Karnofsky) or others. Tumor characteristics may include staging (e.g., tumor-node-metastasis (TNM) staging according to the American Joint Committee on Cancer, AJCC), size, shape, number, location, histology, or others. Treatment information may include regime, dose, time, type, medicine, or others.

Imaging information may include gross tumor volume (GTV), standard uptake value (SUV), or others.

The methods are implemented with the system of FIG. 1, or a different system. The same or different systems may perform creating and applying the models. For example, one computer is used for development, and a different computer is used for applying the developed models. The models may be developed, and then sold or otherwise distributed for application by others. As another example, the use of the developed models is charged. Users request predictions from the developer, so the model is applied by the same computer used for development or by different computer controlled by the developer.

The acts are performed in the order shown or a different order. Additional, different, or fewer acts may be provided. For example in FIG. 3, acts 20, 22, and 24 are not provided. FIGS. 3-5 represent application of models. In alternative embodiments, acts 28, 42, and 52 represent creation of the model to predict rather than prediction.

One or more of the models are created. The model is created as discussed above, such as machine learning using a training data set or by programming based on data from a training set. The models may be created using any type of feature vector. Different feature vectors may be attempted to select a more deterministic group of features. Any number of patients may be included in the training data. For limited training data sets, random selection of training and testing data may be used in many iterations to create a more reliable model. The data is labeled as appropriate for the desired outcome, such as indicating survival and/or a particular level of side-effects. The machine-learning algorithm or algorithms are selected. Any now known or later developed algorithm and process for training may be used.

The training information corresponds to the information used for application of the model. Uptake image information (e.g., change in uptake without consideration of structure other than the tumor) is obtained with any desired additional information, such as dose, clinical information, application information, or other data. Blood biomarker information is obtained with any desired additional information. Bullae information is obtained with or without other additional information. The models may be combined or maintained separately.

The created model or models are validated. A five-fold or other cross validation is performed on patient-data. A leave-one-ut approach may be used. Any validation may be used.

Once created, the model or models are incorporated onto a computer, such as into hardware, software, or both. The incorporation allows operating, with a processor, combined models or a single model. Values for the feature vectors of the models are obtained. The medical record, functional imaging data, and/or other source provide values for a specific or individual patient. The model is applied to the individual patient information.

In acts 26, 40, and 50, information is received. The information is obtained from a scanner, such as uptake or bullae values, or from a blood test, such as blood biomarkers. Alternatively, the information is obtained from memory, such as previously acquired data transferred from a PACS database or a computerized patient record.

The feature information is received in response to a request. For example, the processor 12 requests acquisition of the data by a scanner or from a database. In response, the requested information is transferred to and received by the processor 12. Alternatively, the information is pushed to the processor 12. The receipt may occur in response to user input or without direct user input.

Other feature vector information is received. The data input corresponds to the predictors or variables used by the models. For example, clinical values are received.

The data is input manually. Alternatively, the data is mined from a database. A processor mines the values from a medical record of the individual patient. For example, the mining discussed in U.S. Published Application No. 2003/0120458, the disclosure of which is incorporated herein by reference, is used. Structured clinical data is mined from unstructured and structured information. If values are available from unstructured data, the values may be mined by searching or probabilistic inference. Other mining may be used, such as acquiring data from a structured computerized patient record (CPR). The mined and/or manually input values are applied to the models to obtain a prediction.

Where a value for an individual patient is not available, a value may be assumed, such as using an average. Alternatively, the field may be left blank. For example, one of the questions asked is whether the patient is a smoker or not. If there is no evidence provided in the patient record if the user is a smoker, then the system leaves this blank or records that the user is a smoker, since the prior probability (based on the percentage of smokers) suggests that the lung cancer patient is probably a smoker.

In acts 28, 42, and 52, a probability is determined. The probability predicts side-effects and/or survivability. The probability is predicted as a function of the input feature vectors, such as the blood biomarkers, bullae, or uptake values. The patient specific information is input to the model as values for variables of the feature vector. Clinical factors may include gender, overall stage, gross tumor volume (GTV), performance status (WHO-ps), histology, age, nicotine use, chemotherapy, forced expiratory volume in 1 sec, T-stage, and/or other variables. The patient or tissue response is modeled as a function of the probability of side-effects or survivability given the input feature values. The feature values indicate reaction to therapy.

The model may be for any type or combination of types of treatment. Treatment may be a lack of further action, chemotherapy, type of drug, amount of drug, radiation, type of radiation, radiation timing, or other treatment, or treatment combination.

The model indicates the likelihood of side-effects or survivability a given period after radiation therapy. The application results in one or more probabilities.

In acts 30, 44, and 54, the likelihood from the prediction is output. The likelihood is output to a display. The display is an image of a report indicating the likelihood with or without any corresponding parameters, such as the term (e.g., two year survival). A table, graph, or other output may be provided. Different likelihoods given different values of one or more variables (e.g., features or models) may be output. The image represents a possible condition of the patient and associated probability of that condition.

The output is to a display, such as an electronic display or a printer. The output may be stored in memory or transferred to another computer. In one embodiment, the likelihood information is output for use with a radiotherapy Treatment Planning System (TPS), in order to optimize the radiation treatment. For example, a dose level with the greatest survivability for a given patient is identified. The dose information is included in a treatment plan. The doses are fractionalized, and the treatment information is transferred to the linear accelerator. In response, the linear accelerator applies radiation to the tumor regions.

Referring specifically to FIG. 3, a method for predicting RILI from bullae information is shown. As most patients with lung cancer are current or former smokers, the patients have a high incidence of emphysema. This disease forms large air-filled cavities within the lungs called bullae. Bullae may be formed for other reasons. Because of the density differences with the surrounding lung tissue, bullae may be visualized on CT scans. Bullae are non-functional lung tissue. Dose is determined based, at least in part, on the amount of tissue assumed to be in a lung volume. Bullae add noise to the current calculations of dosimetric parameters by offsetting the amount of tissue.

In act 20, the bullae are segmented from the total lung volume. A medical image of a lung or the lungs of a patient is obtained. For example, CT scans are based on the attenuation of the tissue, thereby on the tissue density. The density of bullae is approximately <−700 HU, which is different than the density of normal lung tissue. The CT image is filtered or a threshold is applied. Darker regions (i.e., low-density regions) are likely bullae. By locating the darker regions, the bullae are segmented from the other lung tissue. The density-corrected CT segmentation sorts out air-filled cavities. For example, a Treatment Planning Systems (TPS) is used to segment the bullae.

In act 22, the volume of the bullae is determined. The medical image data represents a volume containing the lungs. The spatial locations or voxels associated with bullae are counted and multiplied by the size of the voxel or spatial location.

The lung volume may also be determined. The lungs may be segmented from other tissue or structures. Any now known or later developed lung volume segmentation and/or calculation may be used.

In act 24, a percentage of the bullae volume to a total lung volume is determined. This ratio may be weighted or a straight ratio. Other functions representing a relative difference may be used. In other embodiments, a lung volume corrected to remove volume associated with bullae is determined.

In act 26, bullae information is received for a patient with a lung tumor. The bullae information is the percentage, bullae volume, bullae corrected lung volume, or other information derived from bullae information for the patient. The presence of bullae in the lung presumes a smaller amount of functional alveoli in the lung. The area of gas exchange may be less. The ventilation of bullae is assumed to be negligible. The percentage of bullae relative to the total Lung Volume is received as a predictor for acute severe (e.g., grade 3 according to CTCv3.0) pneumonitis. The percentage or other bullae information may be used for prediction of acute or late lung injury.

In act 28, radiation-induced lung injury is predicted. The model determines a likelihood of pneumonitis or other damage given radiation or chemotherapy and radiation treatment. In one embodiment, whether grade 3 damage according to CTCv3.0 occurs is predicted. The likelihood of grade 3 toxicity as opposed to lower grades and no damage is predicted. Using the training data, the percentage of patients at or within a range of a given bullae level that had or did not have damage after treatment is determined. In other embodiments, whether any damage occurs, regardless of grade, is predicted. Alternatively, the prediction of likelihood of grade two or higher toxicity is predicated. For example, separate likelihoods of no damage, grade 1 damage, grade 2 damage, and grade 3 damage are determined.

The prediction is made as a function of the bullae information for the patient. The individual's level of bullae is used to predict the individual's likelihood of side-effects. In one embodiment, only the bullae information is used for the prediction. In other embodiments, bullae information and other variables (e.g., clinical, blood biomarker, and/or uptake) are used by the model for prediction.

In one example embodiment, data from multiple (e.g., 73) lung-cancer patients is gathered. The patients have been treated with various schedules of (chemo-) radiotherapy. The data is used to learn one or more data-driven models to predict whether a patient would suffer level 3 radiation-induced acute pneumonitis (grade 3 according to CTCv3.0) or not. Alternatively, the data is plotted to identify a threshold separation of bullae percentage for patients that ended up with grade 3 pneumonitis and those that did not. The available data may be randomly divided into two groups, such as 70% of the data used as a training set and 30% percent as a testing set. In order to obtain more reliable results, the experiments are repeated 1000 times with different patient data being included in the different training and testing sets.

Multiple models may be learned to distinguish the best or an acceptable model and associated features. For example, the least cost model with sufficient accuracy may be merely charting the bullae percentage to damage probabilities rather than including other features in a more complex data driven model.

In act 30, a likelihood of the radiation-induced lung injury is output. The prediction from act 28 is provided to the medical professional and/or patient. Decisions on treatment and lifestyle given the lung cancer prognosis may be made, at least in part, on the chances for side-effects specific to the patient.

Figure 6:
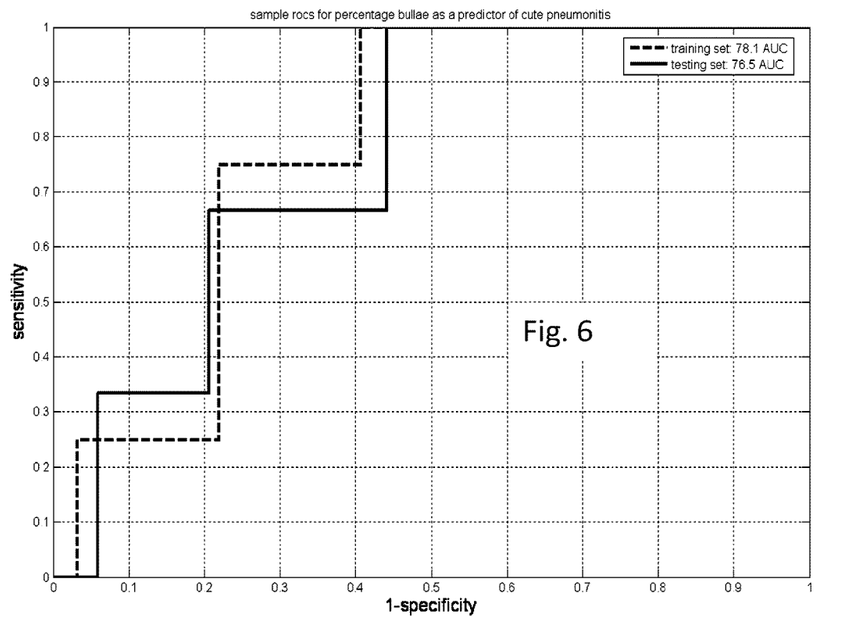
FIG. 6 is an example receiver operating characteristic (ROC) for modeling with Bullae information.

The decision may be guided, at least in part, by the accuracy of the prediction. Given the 73 patient data set discussed above, the results reported below are an average over the 1000 runs. Performance of the model is expressed as the AUC (Area Under the Curve) of the Receiver Operating Characteristic (ROC) curve. The maximum value of the AUC is 1.0, indicating a perfect prediction model. A value of 0.5 indicates that patients are correctly classified in 50% of the cases (e.g., as good as chance). As shown in FIG. 6, a predictive model is trained or programmed using only the percentage bullae variable. The AUC for this model is (in average) 0.78 (std=0.1) for the training set and 0.78 (std=0.12) for the testing set. FIG. 6 shows the ROCs corresponding to one of the 1000 random splits used to validate the model.

By only using the percentage bullae present on the patient's lung extracted from the CT images, a simple model is provided. The simple model may be comparable and/or outperform models learned by using other traditionally-used predictors for the prediction of acute treatment-induced pneumonitis or lung toxicity.

Referring specifically to FIG. 4, an example method of application of a model used for predicting survivability with blood biomarkers is shown. The analysis of circulating proteins may provide useful additional information about the biological profiles of tumors and their hosts. Blood obtained by venepuncture is accessible for testing and may be monitored over long periods. Moreover, the value of blood biomarkers and imaging parameters is available where extensive tumor tissue sampling is impossible in many cases of lung cancer.

A number of biomarkers may be associated with survival or disease progression. As extensive tumor tissue sampling is often impossible. Blood biomarkers may be useful in predicting survival for lung cancer patients treated with radiation Features leading to better predictions for surgery patients may have a lower or no predictive value for radiation therapy patients. Blood biomarkers may relate directly to tumor characteristics, so may be considered likely predictors for survivability of lung cancer patient after radiation treatment. Blood biomarkers related to hypoxia, inflammation, and tumor load may improve the prediction of two- or other number of year survival of non-small cell lung cancer (NSCLC) patients treated with radiation alone or radiation combined with chemotherapy.

In act 40, blood biomarker information is received for a patient with a lung tumor. The individual patient measurements from blood are received for prediction of the likelihood of survival for the individual patient.

Any now known or later developed blood biomarker may be used. Example, blood biomarkers include Osteopontin (OPN), Carbonic Anhydrase 9 (CA9), Interleukin-6 (IL6), Interleukin-8 (IL8), Carcino-embryonic Antigen (CEA) and Cytokeratin Fragment 21.1 (CYFFA). Different, fewer, and/or additional blood biomarkers may be measured, such as lactate dehydrogenase (LDH). LDH, CA9, and OPN relate to hypoxia. IL-6 and IL-8 relate to inflammation. CYFRA 21-1, CEA and OPN relate to tumor load. Values of blood biomarkers may be used directly, mathematical transformations may be applied (e.g., logarithms), or ratio's may be calculated.

Before the start of the radiotherapy treatment, blood samples are collected, processed and stored in a standardized manner. The plasma or serum level of the investigated proteins is determined in all specimens using commercially available enzyme-linked immunosorbent assays (ELISAs) in line with the manufacturers' instructions. Other assays or tests may be used. The blood samples are analyzed simultaneously or at different times.

In act 42, survivability of the patient after radiotherapy is predicted. The prediction uses a machine-learned model. For example, clinical data from 403 inoperable NSCLC patients, stage I-IIIB, treated with curative intent with (chemo) radiation is collected. Blood samples are available for 82 patients. As another example, clinical data is collected from 85 inoperable NSCLC patients (stages I-IIIB) treated with curative intent with radiotherapy alone or combined with chemotherapy. In another example, 142 stage I-IIIB NSCLC patients who have not undergone surgery treatment are treated with curative intent. Data is collected prospectively, ensuring standardization of data collection and high data quality.

A two-norm Support Vector Machine may be used to build a model. Other machine learning algorithms may be used. Multiple models may be created to test for the most accurate. For example, one prognostic model uses only clinical factors (e.g., no blood biomarkers), and another prognostic model uses the clinical factors and blood biomarkers. Performance of the models is expressed as the AUC (Area Under the Curve) of the Receiver Operating Characteristic (ROC) and assessed using leave-one-out (LOO) cross-validation. In addition, a risk score may be calculated and a nomogram, a graphical representation of the risk score, may be made for practical use.

The model is trained to predict as a function of the blood biomarker information for the patient. Different models may be trained for different combinations of blood biomarkers. For example, osteopontin corrected for creatinine clearance, interleukin-8, and carcino-embryonic antigen may be used together for a model. The model may be trained to include other features, such as WHO performance status, a number of positive lymph node stations, and a gross tumor volume. The values for these features may be derived using any technique.

For example, the gross tumor volume is derived from primary and nodal gross tumor volumes. In one embodiment, the primary gross tumor volume ($GTV_{primary}$) and nodal gross tumor volume ($GTV_{nodal}$) are calculated based on pre-treatment fluorodeoxyglucose positron emission tomography (FDG PET) CT scan, using a radiotherapy treatment planning system. The sum of $GTV_{primary}$ and $GTV_{nodal}$ provides the gross tumor volume feature. A mathematical transformation may be applied to the GTV (e.g. logarithmic transformation).

As another example, the number of positive lymph node stations is derived from a PET scan. The number shown by the PET scan is assessed by a nuclear medicine specialist or a determined by an algorithm. T-stage and N-stage are assessed using pre-treatment CT, PET, mediastinoscopy, and endobronchial ultrasound (EBUS) or endoscopic ultrasound (EUS) when applicable. For patients treated with sequential chemotherapy, stage and number of positive lymph node stations are assessed using pre-chemotherapy imaging information.

The features and model are used to predict survival at any time. For example, the likelihood of surviving two years after radiation therapy is predicted by the model. Overall survival is defined as the duration between the start of radiation therapy and the date of death, but may be defined by other periods.

To derive the likelihood of survival, the machine learning uses the training data. In the training data, the patients are treated using CT-based radiotherapy planning. No elective nodal irradiation is performed, and irradiation is delivered five days per week. Any treatment plans may be used. For example, two different radiotherapy regimes are applied. The first group includes a plurality of patients, who receive either 70 Gy (stages I-II) or 60 Gy (stage III) in daily fractions of 2.0 Gy. The second group includes another plurality of patients, who receive from 54.0 to 79.2 Gy delivered in fractions of 1.8 Gy twice daily, depending on the mean lung dose or spinal cord dose constraint.

For statistical analysis, the Kaplan-Meier method is used for univariate survival analysis. Blood biomarker concentrations are dichotomized using the median value as a cutoff point. The log rank test is applied to assess differences between groups.

To build a multivariate prediction model for two-year survival, 2-norm support vector machines are used. Survival outcome is calculated from the start of the radiotherapy treatment. The mean value of a variable is input if the value is missing. A logarithmic transformation is applied to obtain more symmetrically distributed data for the blood biomarkers.

A multivariate model, built on a large patient population and externally validated, may be used as a baseline model. The model uses five clinical features: sex, WHO performance status (WHO-PS), forced expiratory volume ($FEV_1$), number of positive lymph node stations (PLNS), and gross tumor volume (GTV). To assess the added prognostic value of the blood biomarkers, the baseline model is extended with the blood biomarkers mentioned above.

A combinatorial variable selection procedure is performed to obtain the 'best subset' of blood biomarker variables. The best subset may be defined as the combination of biomarkers which resulted in the highest area under the curve (AUC) of the receiver operating curve (ROC), assessed by leave-one-out (LOO) cross validation.

The variable selection procedure may result in the selection of three biomarkers, but more or fewer may be selected. The coefficients and confidence intervals are calculated using a bootstrap procedure, repeated 1000 times, but other procedures may be used. The coefficients are then multiplied by a correction factor to obtain odds ratios. The patient group may be split into three subgroups based on tertiles of the probability score, and Kaplan-Meier curves are made to assess differences in survival of the subgroups, but other subgroups or number of subgroups may be used. The analysis is performed with R, version 2.5.1 (R Foundation for Statistical Computing, Vienna, Austria) and Matlab, version 7.0 (MathWorks, Natick, Mass.), but other analysis programs may be used.

Figure 7:
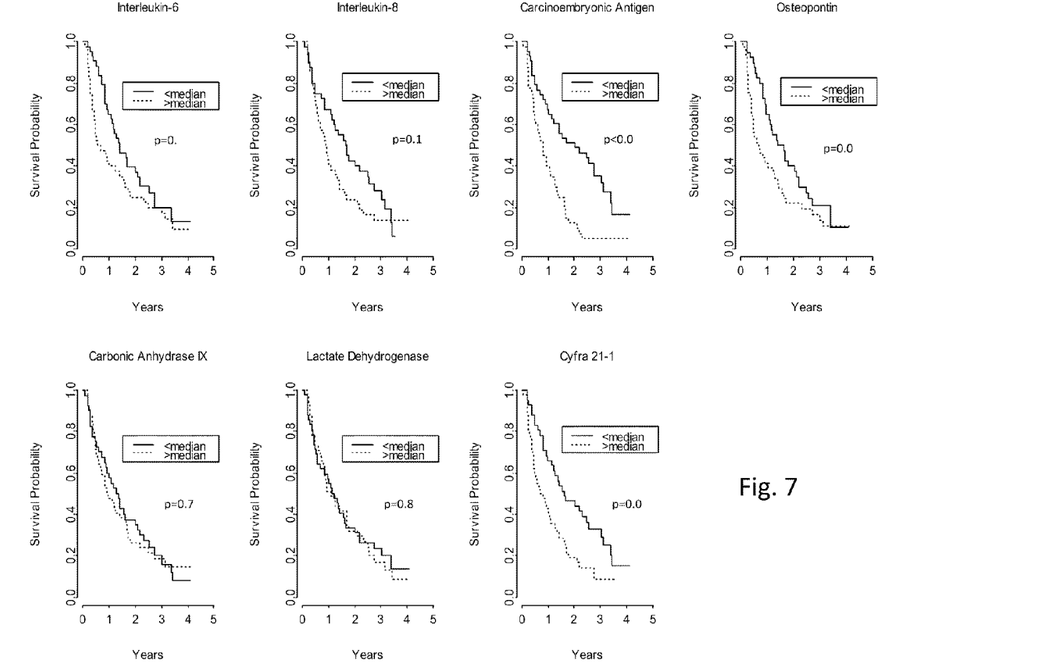
FIG. 7 shows Kaplan-Meier curves for sample blood biomarkers.

The patient characteristics of an example study population are shown below in Table 1. Because of a lack of follow-up information for two patients, 83 patients are included in the survival analysis. The median follow-up is 38 months (range 28-49 months), the median survival 13 months, and the two-year survival for the whole patient group 33%. The results of the blood biomarker measurements are set out below in Table 2. The log rank test shows statistically significant results for CEA and CYFRA 21-1 ($p<0.001$ and $p=0.005$ respectively). Higher CEA and CYFRA 21-1 levels may be associated with a lower chance of survival. The same trend may be observed for the other biomarkers, but the log rank test may not yield statistically significant results. Kaplan-Meier curves are shown in FIG. 7.

TABLE 1

Patient characteristics

| | all patients (n = 85) |
|---|---|
| sex | |
| male | 67 (78.8%) |
| female | 18 (21.2%) |
| age | 42-84 years (mean, 68 years) |
| WHO-PS | |
| 0 | 26 (31.0%) |
| 1 | 48 (57.1%) |
| ≧2 | 10 (11.9%) |
| CCI | |
| 0 | 24 (28.9%) |
| 1 | 37 (44.6%) |
| 2 | 14 (16.9%) |
| ≧3 | 8 (9.6%) |
| weight loss | |
| <10% | 61 (84.7%) |
| ≧10% | 11 (15.3%) |
| FEV$_1$ (%) | 27-120 (mean, 71%) |
| histology | |
| SCC | 33 (38.8%) |
| adenoca | 15 (17.6%) |
| large cell ca | 28 (32.9%) |
| other | 2 (2.4%) |
| no histology | 7 (8.2%) |
| clinical stage | |
| I | 14 (16.5%) |
| II | 8 (9.4%) |
| IIIA | 17 (20.0%) |
| IIIB | 46 (54.1%) |
| gross tumor volume | 1-660 ml (mean, 92 ml) |
| PLNS | |
| 0 | 28 (35.9%) |
| 1 | 12 (15.4%) |
| ≧2 | 38 (48.7%) |
| chemotherapy | |
| no | 26 (30.6%) |
| yes | 59 (69.4%) |
| EQD$_{2,T}$ (Gray) | 44.3-76.6 (mean, 5667 Gray) |

TABLE 1-continued

Patient characteristics

| | all patients (n = 85) |
|---|---|
| fractionation scheme | |
| once daily | 43 (50.6%) |
| twice daily | 42 (49.4%) |
| OTT (days) | 16-60 (mean, 34) |

Abbreviations:
WHO-PS = World Health Organization performance status;
CCI = Charlson comorbidity index;
FEV$_1$ = forced expiratory volume (1s);
SCC = squamous cell carcinoma;
PLNS = number of positive lymph node stations (assessed on PET);
EQD$_{2,T}$ = total tumor dose corrected for fraction size and overall treatment time;
OTT = overall treatment time

TABLE 2

Biomarkers in blood plasma

| | Concentration (n = 85) | | | |
|---|---|---|---|---|
| | Median | Mean | SD | Range |
| LDH (U/l)* | 379 | 392 | 104 | 136-903 |
| CA IX (pg/ml)* | 231 | 364 | 397 | 59-2477 |
| Interleukin 6 (pg/ml)** | 6.2 | 7.9 | 6.1 | 2.0-40.8 |
| Interleukin 8 (pg/ml)** | 9.4 | 12.1 | 11.5 | 5.0-88.4 |
| CEA (ng/ml)** | 4.1 | 15.0 | 45.3 | 0.6-304.0 |
| CYFRA (ng/ml)** | 1.6 | 4.3 | 7.8 | 0.2-49.5 |
| Osteopontin (ng/ml)* | 98.1 | 111.3 | 42.6 | 50.0-244.3 |

Figure 8:
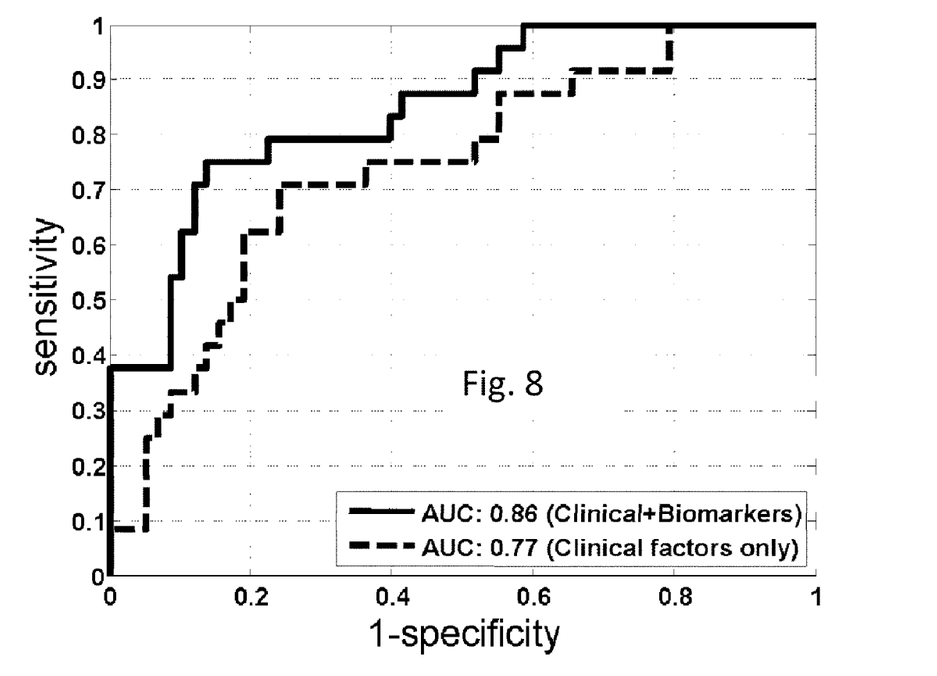
FIG. 8 is an example receiver operating characteristic (ROC) for modeling with blood biomarker information.

Abbreviations:
LDH = lactate dehydrogenase;
CA IX = carbonic anhydrase IX;
CEA = carcinoembryonic antigen;
CYFRA = cytokeratin fragment 21.1
*measurements performed using plasma
**measurements performed using serum The baseline model has five variables: sex, WHO-PS, FEV$_1$, GTV, and PLNS. The variables available for the extended model are CEA, CA IX, OPN, CYFRA 21-1, LDH, IL-6, IL-8. After the variable selection procedure, the final model may include the five variables included in the baseline model and three additional biomarkers: CEA, IL-6 and CA IX. The most powerful prognostic factors for two-year survival may be GTV, CEA and WHO-PS. The AUC of the final model is 0.86 (95% CI 0.76-0.94), assessed by LOO cross validation. The baseline model, applied to the study population of 83 patients, yields an AUC of 0.77 (95% CI: 0.64-0.88) (FIG. 8). The difference between the two models is statistically significant ($p<0.001$).

Figure 9:
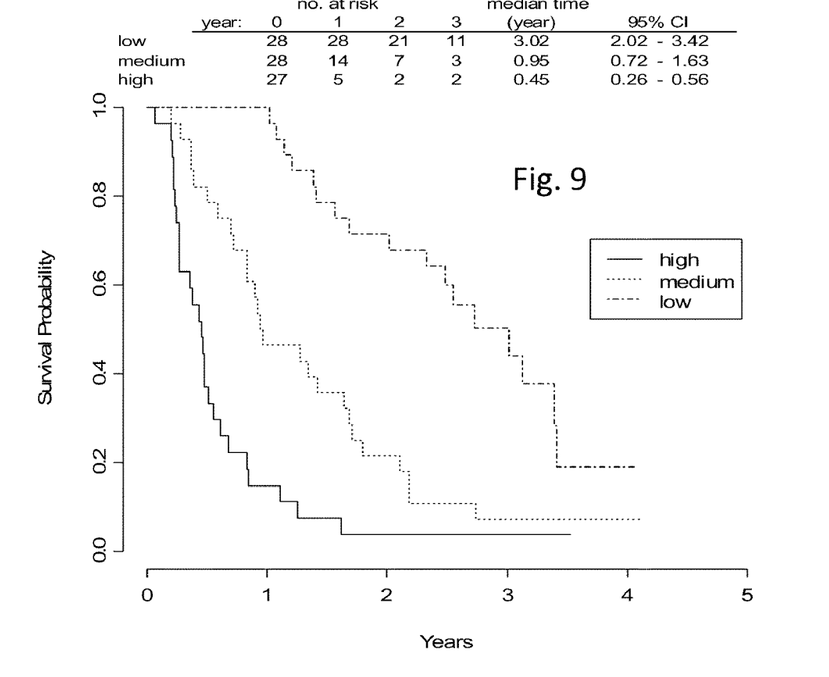
FIG. 9 shows example survival prediction by risk category.

The improved performance may be due to any factor, such as being mainly due to the prognostic value of CEA, while the contribution of IL-6 as well as CA IX is limited. The odds ratios for the variables included in the multivariate model are shown in Table 3. Splitting the study population into three subgroups based on tertiles of the probability score results in the identification of low, medium and high-risk groups. The two-year survival is 71% (95% CI 51%-85%) for the low risk group, 21% (95% CI 9%-38%) for the medium risk group, and 4% (95% CI 0.3%-16%) for the high-risk group (FIG. 9). According to this probability score, six patients with a clinical T4 tumor (26.1% of all T4 patients), five with a clinical N3 stage tumor (20.0% of all N3 patients), five with a clinical stage IIIA (29.4% of all IIIA patients), and ten with a clinical stage IIIB (22.7% of all IIIB patients) are included in the low risk group.

TABLE 3

Odds ratios for survival at two-year timepoint

| Variable | Coefficient | Odds ratio | 95% CI | P |
|---|---|---|---|---|
| sex | | | | 0.312 |
| male | | ref | | |
| female | 0.98 | 2.66 | 0.40-18.23 | |
| WHO-PS | | | | 0.076 |
| 0 | | ref | | |
| 1 | −1.16 | 0.31 | 0.09-1.37 | |
| ≧2 | −2.32 | 0.10 | 0.01-1.88 | |
| $FEV_1$ | −0.01 | 0.99 | 0.95-1.03 | 0.584 |
| PLNS | | | | 0.108 |
| 0 | | ref | | |
| 1 | −0.47 | 0.63 | 0.36-1.10 | |
| 2 | −0.93 | 0.39 | 0.13-1.21 | |
| 3 | −1.40 | 0.25 | 0.05-1.34 | |
| ≧4 | −1.86 | 0.16 | 0.02-1.48 | |
| GTV (ml)* | −1.30 | 0.27 | 0.13-0.53 | <0.001 |
| CEA* | −1.25 | 0.29 | 0.15 0.56 | <0.001 |
| IL-6* | −1.04 | 0.35 | 0.09 1.57 | 0.143 |
| CA IX* | −0.70 | 0.49 | 0.16-1.54 | 0.211 |

Figure 10:
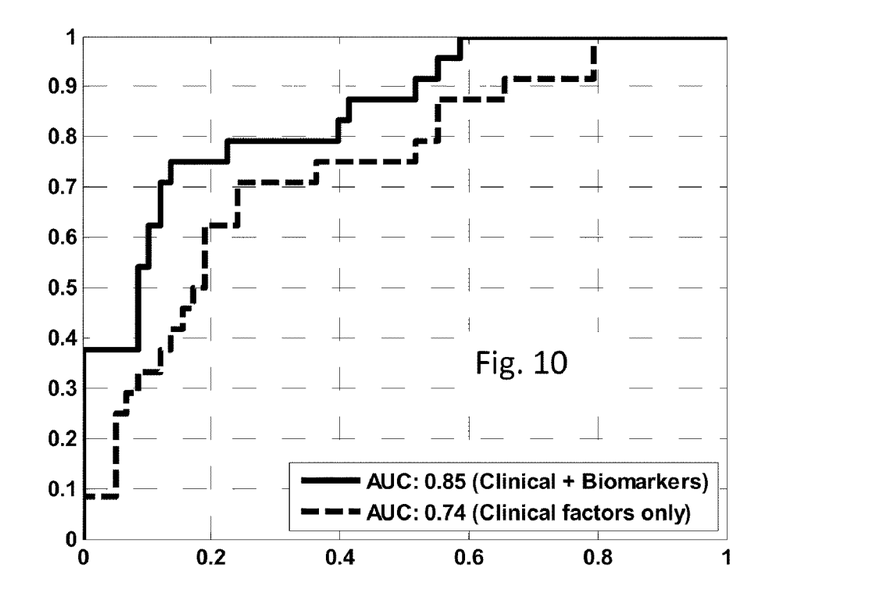
FIG. 10 is another example receiver operating characteristic (ROC) for modeling with blood biomarker information.

Abbreviations:
CI = confidence interval;
WHO-PS = World Health Organization performance status;
$FEV_1$ = forced expiratory volume in 1 second;
PLNS = number of positive lymph node stations;
GTV = gross tumor volume;
CEA = carcinoembryonic antigen;
IL-6 = interleukin 6;
CA IX = carbonic anhydrase IX
*logarithmic transformation used for analysis A multivariate model, built on a large patient population (n=322) and externally validated, is used as a baseline model in another example. An extended model is created by selecting additional biomarkers. FIG. 10 shows the performance for this example.

In act 44, the survivability is output. Survivability may be a probability, other likelihood, a time (e.g., 3 year survival verses 2 year survival), or any other indication of survival based on the prediction for the individual patient.

One example model, based on 403 patients and using clinical factors, consists of gender, WHO performance status, forced expiratory volume, number of positive lymph node stations and gross tumor volume. The LOO AUC is 0.75 (95% CI 0.70-0.82), while application of the model to external or other datasets yields an AUC of 0.75 and 0.76 respectively. By splitting the cohort into three subgroups, based on the risk score, high, medium and low risk groups are identified. The 2-year survival is 66% (95% CI 54%-78%) for the low risk group, 29% (95% CI 21%-37%) for the medium risk group and 14% (95% CI 5%-23%) for the high-risk group. The output may indicate the risk group for a given patient.

In another example model based on 82 patients, the prognostic model includes three additional blood biomarker factors: OPN, IL8 and CEA. The LOO AUC is 0.83 (95% CI 0.76-0.94), which is significantly better than the prognostic model using only clinical factors and based on the same 82 patients (AUC 0.71, 95% CI 0.60-0.87): p<0.001. The model, using clinical factors, successfully estimates 2-year survival of NSCLC patients and the performance is good. Combining blood biomarkers with clinical factors may yield a significantly better performance than using clinical factors only.

In the example of FIG. 8, the baseline model uses a feature vector of sex, WHO performance status, forced expiratory volume, number of positive lymph node stations and gross tumor volume, and yields a LOO AUC of 0.77 (95% CI: 0.64-0.88). The extended model includes three additional biomarkers (CEA, IL-6 and CA IX), and results in a LOO AUC of 0.86 (95% CI 0.76-0.94). 0.86 is significantly better than the performance (0.77) of the baseline model (p<0.001). In this example study, the performance of a prognostic model for two-year survival of NSCLC patients treated with (chemo) radiotherapy is improved by incorporating blood biomarker information.

Of the blood biomarkers, CEA serum levels are a prognostic factor in colorectal, breast and lung cancer. CEA is a glycoprotein, which is expressed in both normal and tumor tissue. In normal tissue, CEA is excreted into the lumen of an organ, while in tumor tissue, due to disturbed differentiation, CEA is expressed on the whole cell surface and excreted in intercellular spaces, allowing access to blood or lymphatic vessels. As the tumor size increases, more CEA accumulates in the blood. Patients with an increased CEA level have both a shorter disease-free survival and a lower overall survival than those with normal CEA levels.

A higher level of IL-6 may be indicative of a lower chance of survival. However, higher blood levels of inflammatory markers may also be associated with lower survival in patients with chronic obstructive pulmonary disease (COPD). As COPD is a very common comorbidity condition in lung cancer patients, this might offer an alternative explanation.

CA IX may be a surrogate marker of hypoxia. It has recently become possible to measure the concentration of CA IX using blood samples. A higher CA IX level may be associated with a lower chance of survival.

Other biomarkers may have prognostic value. By incorporating multiple blood biomarkers into a machine-learned model, complex interrelationships may be derived and used to better predict survivability given the data for a specific patient.

In the examples above, biomarker measurements are performed on pre-treatment blood samples. Given the complex interplay between tumor processes such as hypoxia, inflammation and acidosis, treatment characteristics, and the expression of biomarkers, other models may incorporate measurements at several time points to monitor biomarker levels and output prognostic information based on fluctuations or difference over time.

Although the selection procedure for the baseline model includes a number of treatment characteristics, such as total treatment dose (TTD), overall treatment time (OTT), equivalent radiation dose corrected for fraction size and time ($EQD_{2,T}$), and chemotherapy, their association with survival may not be sufficiently strong to be selected in the model. This contradicts clinical trials, which have reported a statistically significant influence of treatment parameters (e.g. sequential chemotherapy and OTT) on survival rate. However, these effects are often small and the results are usually obtained using a highly selected study population. By machine training with a representative training data set, other variables may be selected with more prognostic value in combination. In other embodiments, dose information is selected.

More accurate survival prediction is possible using blood biomarkers. Different models with or without the same feature vectors may be used for different sub-groups of patients for more accurate prediction. Selecting subgroups of patients which might benefit most from a more accurate prediction may improve the treatment decision-making process for these patients as well as restricting the extra costs of biomarker measurement.

Referring specifically to FIG. 5, an example of application of a model used for predicting complication with uptake is shown. Uptake includes an average, median, variance, or other quantity derived from an image or images representing uptake of an imaging agent by the tumor. Other features may be included in the feature vector. Additional, different, or fewer acts may be provided.

In act 50, information representing uptake of an imaging agent for a patient with a lung tumor is received. For example, the information representing the uptake for the patient is positron emission tomography imaging with fluorodeoxyglucose (FDG). FDG as a glucose analog, is taken up by high-glucose-using cells such as tumor cells, such that the PET-FDG image identifies glucose metabolism of the tumor. Other imaging agents for identifying any function of the tumor may be identified. Protein tags or other binding agents may be used to identify function. Contrast agents may be used. More than one type of function may be identified, such as using multi-spectrum approaches.

The uptake information is standardized. Standardization allows comparison between different patients or for a same patient at different times. The uptake values may be standardized based on a known or likely healthy tissue region. For example, a healthy tissue in the PET-FDG image is selected, and the mean of the uptake in the selected region is set as a baseline. The standardized uptake values are deviations from the baseline. The dynamic range may be remapped.

The functional information shows different function at different portions of the tumor or other tissue. In one embodiment, the functional imaging data includes voxels representing three-dimensions. Each voxel is treated as a different location. The scan settings determine the voxel size. In other embodiments, the region or location is larger than the voxel. Data from multiple voxels is combined to determine the functional information for that location of the tissue. The SUV from these different locations may be combined into a single value, such as an integral of SUV. The value may account for a relation to tumor or lung size.

The uptake information, such as the imaging data of the uptake of an agent, is acquired from a time before a current treatment of the patient. For example, the functional information is acquired hours, days, or weeks prior to therapy. Alternatively, the functional information is acquired during treatment, such as between fractions of a therapy plan or interleaved with the application of therapy.

In act 52, radiation-induced lung injury is predicted as a function of the information representing the uptake for the patient. The feature vector information, including uptake, for the patient is applied to a machine-trained or other model. The model determines a likelihood of side-effects given the individual patient data.

In one embodiment, the model is trained based on a change in uptake during radiation therapy. For example, an FDG-PET-CT scan is made on day 0, day 7, and day 14 after initiation of radical radiotherapy for 18 patients for training data and for a current patient. The scan is performed early in the therapy to allow use of the prediction to change or adapt the radiation therapy. Any information representing the change may be used, such as a difference in volume of uptake above a threshold. In one embodiment, the standardized uptake value (SUV) information is used to determine a volume of sufficient uptake in the tumor. The SUV volume is subtracted from or used in a ratio with the gross tumor volume. The high-uptake or sufficient SUV regions are defined as the regions of the lung with a SUV>x, with x ranging from 1 to 2.5. Other values may be used.

The scanning for one day may result in different lung volumes. In one embodiment, lung volume influences are removed. The volumes of high uptake regions (SUV volume) and gross tumor volume are normalized for the total lung volume of that day (e.g., volume represented in the particular scan). Other or no normalization may be used.

In the example model machine-trained from data for 18 patients, six of the patients develop RILI≧grade 2. The delta SUV (>1.5) between day 14 and day 0 may be highly predictive for the risk at RILI (AUC=0.83), using an LOO algorithm. Blood biomarkers are not used as part of the feature vector, but may be.

In act 54, a likelihood of the radiation-induced lung injury is output. The likelihood is determined as a function of or from the predicting. For example, the likelihood is a chance of pneumonitis or other lung toxicity from radiation therapy according to the model trained from data for other patients.

The increase of FDG uptake in the high-uptake (SUV>1.5) regions of the normal lung during radiotherapy within the first two weeks may be highly predictive (AUC=0.83) for subsequent clinical RILI. The output prediction for a given patient may allow for informed choices, more likely avoiding RILI.

Various improvements described herein may be used together or separately. Any form of data mining or searching may be used. Although illustrative embodiments have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A system for modeling side effects for lung cancer patients, the system comprising:
   an input configured to receive lung cancer patient information representing at least lung bullae information of the lung cancer patient;
   a processor configured to apply a model to the lung cancer patient information, to generate at least a side-effects prediction for the lung cancer patient as a response to radiation therapy, wherein the processor is configured to determine a ratio of the lung bullae to a lung volume, and wherein the model is applied with only said ratio to the side-effects prediction, the side-effects prediction comprising pneumonitis; and
   a display configured to output the side-effects prediction generated from the model for the lung cancer patient.

2. The system of claim 1 wherein the input is configured to receive the lung bullae as the lung cancer patient information, wherein the processor is configured to determine a ratio of the lung bullae to a lung volume, and wherein the model is applied with only the ratio to generate the side-effects prediction, the side-effects prediction comprising pneumonitis.

3. The system of claim 1 wherein the model comprises a model for non-small cell lung cancer for the radiation therapy.

4. The system of claim 1 wherein the model is a machine-learned model.

5. The system of claim 1 wherein the output of the model represents a probability.

6. The system of claim 1 wherein the side-effects prediction comprises a radiation-induced lung injury prediction.

7. The system of claim 6 wherein the side-effects prediction comprises a grade of the radiation-induced lung injury prediction.

8. The system of claim 7 wherein the side-effects prediction comprises a prediction of grade 3 radiation-induced lung injury occurrence as a function of the bullae information.

9. The system of claim 1 wherein the model generates the side-effects prediction as a function of a feature vector including only the bullae information.

10. The system of claim 1 wherein the model generates the side-effects prediction by segmenting bullae from a medical image of a lung of the patient, determining a bullae volume, and determining a percentage of the bullae volume to a total lung volume, the percentage being the received bullae information.

11. The system of claim 1 wherein the model generates the side-effects prediction by applying a threshold to the bullae information.

* * * * *